United States Patent [19]

Paton et al.

[11] Patent Number: 5,010,503

[45] Date of Patent: Apr. 23, 1991

[54] APPARATUS FOR ACOUSTIC-EMISSION INSPECTION OF ARTICLES

[75] Inventors: Boris E. Paton, Kiev; Vladimir F. Utkin, Dnepropetrovsk; Anatoly Y. Nedoseka, Kiev; Nikolai T. Khromyak, Kiev; Nikolai V. Gorlitsyn, Kiev; Viktor G. Tikhy, Dnepropetrovsk; Evgeny D. Mezintsev, Moscow; Nikolai N. Mezhuev, Dnepropetrovsk, all of U.S.S.R.

[73] Assignee: Institut Elektrosvarki Imeni E.O. Patona Akademii Nauk Ukrainskoi SSR, Kiev, U.S.S.R.

[21] Appl. No.: 449,854

[22] PCT Filed: Apr. 20, 1988

[86] PCT No.: PCT/SU88/00091

§ 371 Date: Dec. 19, 1989

§ 102(e) Date: Dec. 19, 1989

[87] PCT Pub. No.: WO89/10560

PCT Pub. Date: Nov. 2, 1989

[51] Int. Cl.[5] .............................................. G01N 29/04
[52] U.S. Cl. ..................................... 364/569; 364/507; 73/587
[58] Field of Search ............... 364/507, 569, 508, 506; 73/602, 587, 579

[56] References Cited

U.S. PATENT DOCUMENTS 4,459,851 7/1984 Crostack ............................ 73/587
4,562,736 1/1986 Iwasaki ............................... 73/587
4,609,994 2/1986 Bassim et al. ................... 73/587 X
4,641,526 2/1987 Izumi et al. ..................... 73/587 X
4,644,482 2/1987 Juanarena ....................... 73/579 X Primary Examiner—Parshotam S. Lall
Assistant Examiner—S. A. Melnick
Attorney, Agent, or Firm—Lilling and Lilling

[57] ABSTRACT

The apparatus for acoustic-emission inspection of articles has channels each including a series connection of a transducer of acoustic emission signals, positionable on an article under inspection, and an amplifier of electric signals, having connected to its output a unit for measuring the parameters of acoustic emission signals and a shaper of single pulses, of which the output is connected to the first input of a unit for measuring time intervals. The other input of the unit for measuring time intervals of each channel is connected to the output of a clock pulse generator. The output of the clock pulse generator is also connected to the input of a frequency divider. The apparatus further comprises an OR gate of which the inputs, in a number equalling the number of the channels, are connected to the outputs of the shapers of single pulses of each channel, and the output is connected to the third inputs of the units for measuring time intervals in each channel. The outputs of the units for measuring the parameters of acoustic emission signals and of the units for measuring time intervals of each channel are connected to the inputs of a switching device. A computer for processing acoustic emission data is connected to the switching device.

2 Claims, 7 Drawing Sheets

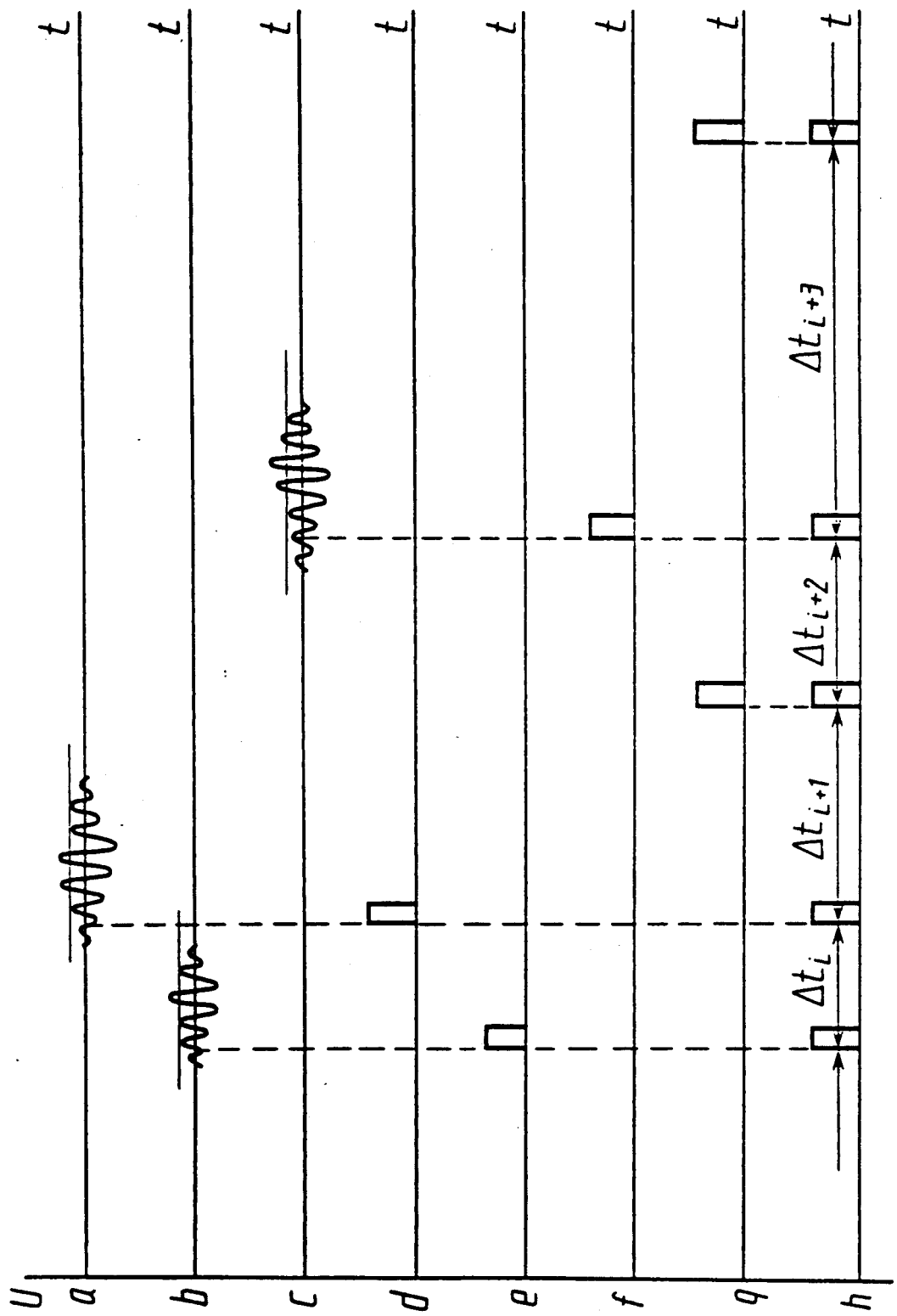

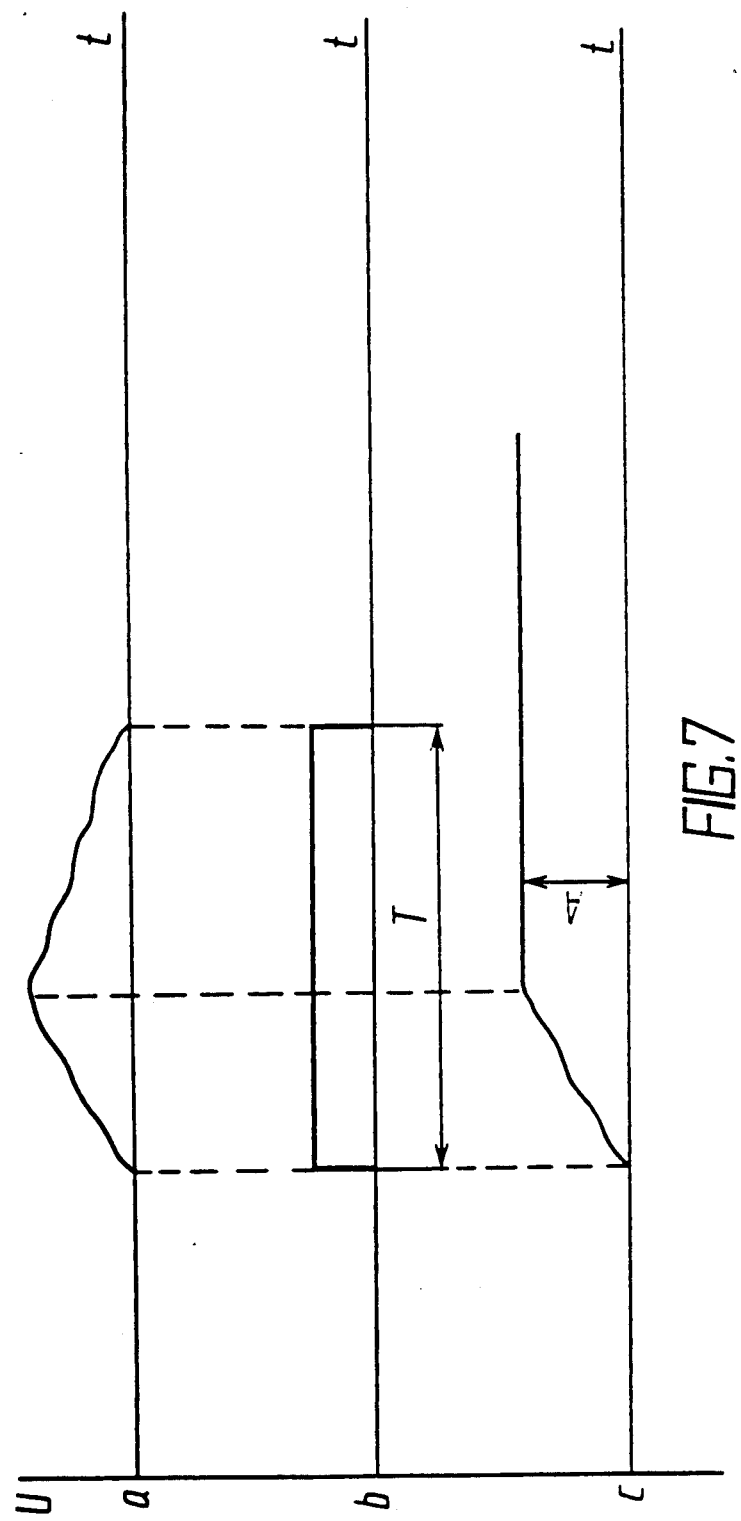

APPARATUS FOR ACOUSTIC-EMISSION INSPECTION OF ARTICLES

BACKGROUND OF THE INVENTION

1. Field of the Invention

The present invention relates to apparatus for nondestructive inspection and testing of articles, and more particularly it relates to apparatus for acoustic-emission inspection of articles.

2. Description of the Related Art

There is widely known an apparatus for acoustic-emission determination of the coordinates of a developing crack in an article, comprising a plurality of channels each including a serial connection of a transducer of acoustic emission signals, positionable on an article, under inspection, and an amplifier of signals of acoustic emission. The outputs of the amplifiers of acoustic emission signals of all channels are connected to the first inputs of an encoder. Connected to the first outputs of the encoder are the first inputs of respective shift registers in a number equalling the number of the channels. The outputs of all shift registers are connected to the inputs of the first OR gate and to the first input of an electronic computing unit having its output connected to the input of a registration unit. The output of the first OR gate is connected to the respective first inputs of the first and second flip-flops. The first output of the first flip-flop is connected to the second input of the encoder. The second output of the first flip-flop is connected to the first input of a counter. The apparatus further comprises a second OR gate of which the first input is connected to the second output of the electronic computing unit, the second input is connected to the first output of the counter, and the output is connected to the second inputs of the respective shift registers, to the second input of the first flip-flop, and to the first input of the third OR gate. The second input of the third OR gate is connected to the third output of the electronic computing unit. The output of the third OR gate is connected to the second input of the second flip-flop.

The apparatus also comprises a series connection of a clock pulse generator and an AND gate, the second input of the electronic computing unit being connected to the output of the second flip-flop, as is the second input of the AND gate, and the third input of the electronic computing unit being connected to the digit outputs of the counter. The third inputs of the shift registers are connected along with the second input of the counter, to the output of the AND gate.

When a developing crack evolves in the article, a signal comes to the transducer of acoustic emission signals, and the code of the channel which has been the first to receive the acoustic emission signal is written in the lower-order digits of the shift registers. Then this code is shifted in the shift registers through the number of digit positions corresponding to the time interval passing before the instant of reception of an acoustic emission signal by another channel, whose code is written in the lower-order digits of the shift registers.

The appearance of the code of the first-mentioned channel at the output of the registers triggers the process of data transfer to the electronic computing unit. The counter counts the number of the digit positions between successive codes written in the shift registers, thus determining the time intervals between the instants of reception of the acoustic emission signals in the respective channels. However, for the apparatus to ensure proper functioning of this data-reading mode, the encoder is inhibited, so that reception of new information is also inhibited. This amounts to a high probability of useful signals of acoustic emission being missed by the apparatus, which significantly impairs the reliability and credibility of the inspection of an article.

Also widely known is an apparatus for determining from acoustic emission signals the coordinates of a crack developing in an article, comprising a plurality of channels each including a series connection of a transducer of acoustic emission signals positionable on an article under inspection and an amplifier of electric signals having its output connected to the respective inputs of a shaper of single pulses and of a unit measuring the parameters of acoustic emission signals. The outputs of the shaper of single pulses and of the unit measuring the parameters of acoustic emission signals are connected to the first and second inputs of the register of the channel. The apparatus further comprises a series connection of a clock pulse generator and a pulse counter having its output connected to the third inputs of the registers of the respective channels. The channels are arranged in groups, the outputs of the registers in each group being united by a common bus serving as a switching device and being connected to the input of a primary data processing unit corresponding to this group. The outputs of the primary data processing units are united by the second common bus and connected to the input of a computer having its output connected to the input of a registration unit.

When a developing crack evolves in the article under inspection, and an acoustic emission signal reaches the channel which is the first to receive this signal, the current time from the commencing of the inspection operation, monitored by the counter, is written into the register of this channel. At the same moment, the register has recorded therein the outcome of the measurement of the parameters of the acoustic emission signal (i.e. its amplitude and duration), and this information is fed to the computer via the switching device. As soon as other channels receive the signal, they also feed their information to the computer. The computer calculates the time intervals between the instants of reception of the acoustic emission signals, computes the coordinates of the source of acoustic emission in the article and assesses its potential hazard.

However, this apparatus would not ensure sufficient reliability and credibility when articles with a high level of inherent activity are inspected. This is explained by the insufficient throughput of the computer which has to handle coded words of an extended size in the appratus being described. To ensure adequate accuracy of computation of time intervals between the instants of reception of acoustic emission signals, the current time should be counted in increments as small as microseconds, and in some cases even as small as fractions of microseconds. However, the maximum value of the current time can be dozens of minutes, hours or even days, depending on the kind of the article under inspection and the test conditions. Thus, the length of coded words representing the current time at the input of the computer can be from 30 to 40 bits, whereas the standard word length of present-day computers is generally from 8 to 16 bits. In other words, the computer of the apparatus being described is doomed to operation (i.e. input, intermediate handling, computation) with words whose length is several times over the standard word length it is rated for. The consequence of the low throughput of the computer can be the loss of acoustic emission information, which, in its turn, affects the reliability and significance of the inspection of an article. Moreover, the apparatus of the prior art being described has an excessive amount of electric connections between its measuring and processing parts, which steps up the noise protection requirements and complicates the designing of the apparatus.

SUMMARY OF THE INVENTION

The problem is solved by an apparatus for acoustice-mission inspection of articles, comprising channels each including a series connection of a transducer of acoustic emission signals positionable on an article under inspection, and an amplifier of electric signals having connected to its output a shaper of single pulses and a unit measuring the parameters of acoustic emission signals, and also a clock pulse generator connected with each channel, a switching unit having its inputs connected to the outputs of the units measuring the parameters of acoustic emission signals and also connected with the shapers of single pulses of the respective channels, and a computer for processing acoustic-emission data, connected to the switching unit, which apparatus, in accordance with the present invention, further includes in each channel a unit for measuring time intervals, having its first input connected to the output of the shaper of single pulses, its second input connected to the output of the clock pulse generator, and its output connected to the input of the switching unit, and also a frequency divider having its input connected to the output of the clock pulse generator and its output connected to the switching unit, and an OR gate whose inputs in a number equalling the number of the channels are connected to the respective outputs of the shapers of single pulses of each channel, and whose output is connected to the third inputs of the respective units for measuring time intervals in each channel.

To enhance still further the reliability of the inspection of articles, it is expedient that the apparatus should comprise an additional unit for measuring time intervals, having its first input connected to the output of the frequency divider and to an additional input of the OR gate, its second input connected to the output of the clock pulse generator, its third input connected to the output of the OR gate, and its output connected to the input of the switching unit.

The disclosed apparatus for acoustic-emission inspection of articles provides for measuring time intervals between the instant of reception of an acoustic emission signal by the transducer of acoustic emission signals of one channel and the instant of reception of the acoustic emission signal by the transducer of acoustic emission signals of another channel, without measuring the current or running time of the reception of each acoustic emission signal, which significantly reduces the length of the coded words at the input of the computer and minimizes the processing time of each acoustic emission signal evolving in the article. In this way the throughput of the measuring part of the apparatus is stepped up, the loss of acoustic-emission data in the inspection of articles with high levels of acoustic emission activity is curtailed, and the reliability of the inspection of such articles is enhanced.

BRIEF DESCRIPTION OF THE DRAWINGS

The present invention will be further described in connection with its embodiments in an apparatus for acoustic-emission inspection of articles, with reference being made to the accompanying drawings, wherein:

FIG. 6 is a chart plotting the voltage versus time at the components of the apparatus embodying the invention;

FIG. 7 is a chart plotting the voltage versus time at the components of the unit measuring the parameters of acoustic emission signals in the apparatus embodying the invention.

DESCRIPTION OF THE PREFERRED EMBODIMENT

Figure 1:
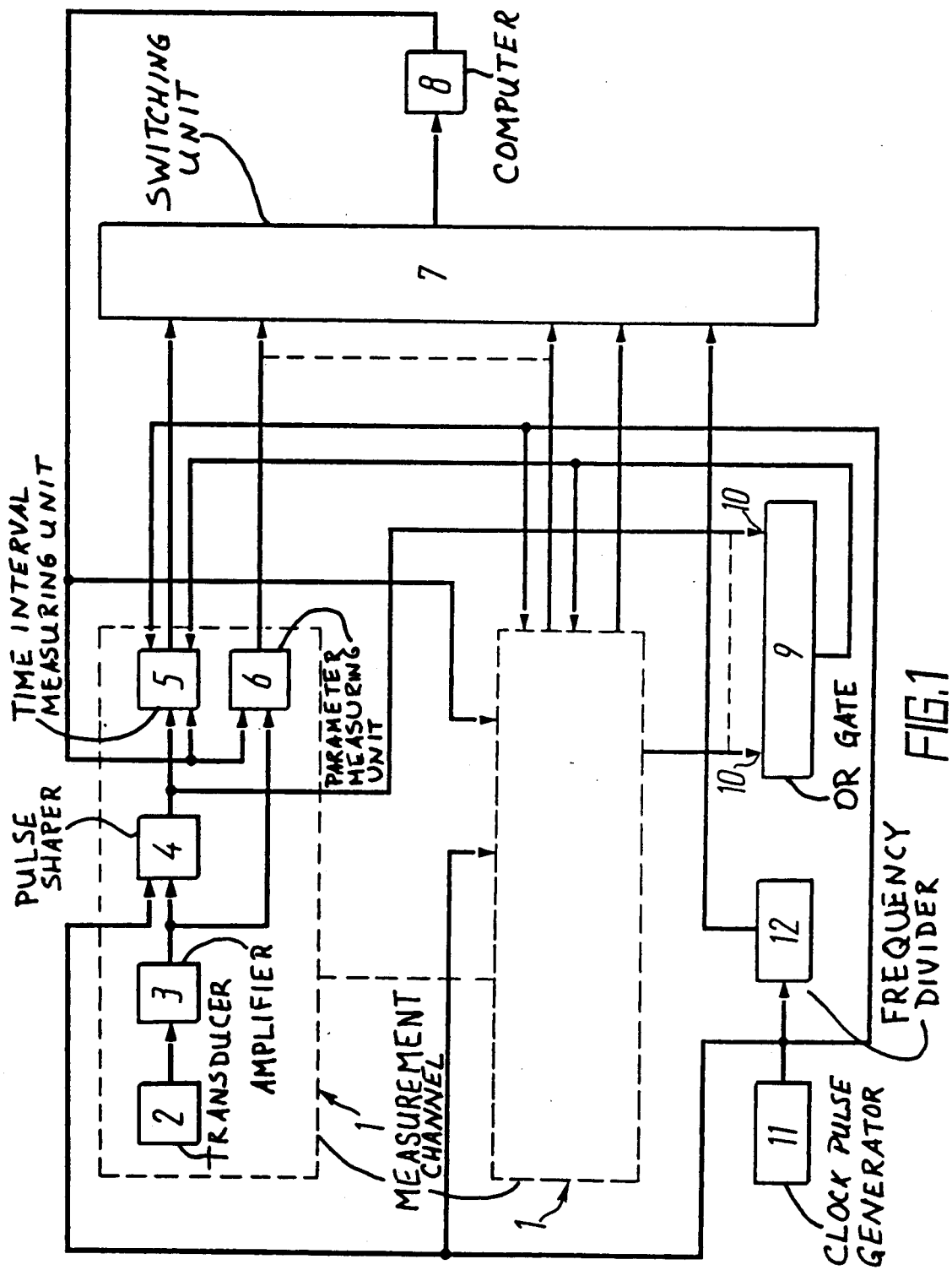
FIG. 1 is a block unit diagram of one embodiment of the apparatus according to the invention.

The apparatus for acoustic-emission inspection of articles comprises a plurality of measurement channels 1 (FIG. 1) in a number dependent on the surface area of the article under inspection, the required accuracy of locating a source of acoustic emission, the expected level of acoustic emission signals in an article, and the attenuation factor of acoustic emission signals in the article. The minimum number of the channels is three, which is defined by the number of measurements necessary for solving the triangulation problem in locating a source of acoustic emission. Each channel 1 includes a series connection of a transducer 2 of acoustic emission signals, an amplifier 3 of electric signals, a shaper 4 of single pulses and a unit 5 for measuring time intervals. The output of the amplifier 3 of electric pulses is connected to the first input of the shaper 4 of single pulses. The output of the shaper 4 of single pulses is connected to the first input of the unit 5 for measuring time intervals.

The output of the amplifier 3 of electric signals has also connected to it the first input of a unit 6 measuring the parameters of signals of acoustic emission.

The piezoelectric transducer 2 of acoustic emission signals of a generally known structure (Greshnikov V.A., Drobot Yu. B. "Akusticheskaya emissiya", 1976, Izdatel'stvo Standartov/Moscow/, pp. 71-76) is fastened to the surface of an article under inspection with an acoustically transparent adhesive, a strapping, a permanent magnet (for articles of ferromagnetic materials), or any other means ensuring reliable acoustic contact with the surface of the inspected article.

The amplifier 3 of electric signal is likewise of a generally known structure (Greshnikov V.A., Drobot Yu. B. "Akusticheskaya emissiya", 1976, Isdatel'stvo Standartov /Moscow/, pp. 76-78).

The outputs of the unit 5 for measuring time intervals and of a unit 6 for measuring the parameters of acoustic emission signals are connected to the inputs of a switching unit 7. The outputs of the switching unit 7 are connected to a computer 8 for processing acoustic-emission data.

The computer 8 is an all-purpose electronic computer of any suitable known structure.

The apparatus further comprises an OR gate 9 having its inputs 10 in a number equalling the number of the channels 1 connected to the outputs of the respective shapers 4 of single pulses.

The apparatus still further comprises a clock pulse generator 11 having its output connected to the respective second inputs of the shapers 4 of single pulses, the second inputs of the time interval measuring units 5 of the respective channels 1, and to the input of a frequency divider 12. The output of the frequency divider 12 is connected to the switching unit 7.

The output of the OR gate 9 is connected to the respective third inputs of the time interval measuring units 5 of each respective channel 1.

The output of the computer 8 is connected to the respective fourth inputs of the time interval measuring units 5 and to the respective second inputs of the units 6 for measuring the parameters of acoustic emission signals.

Figure 2:
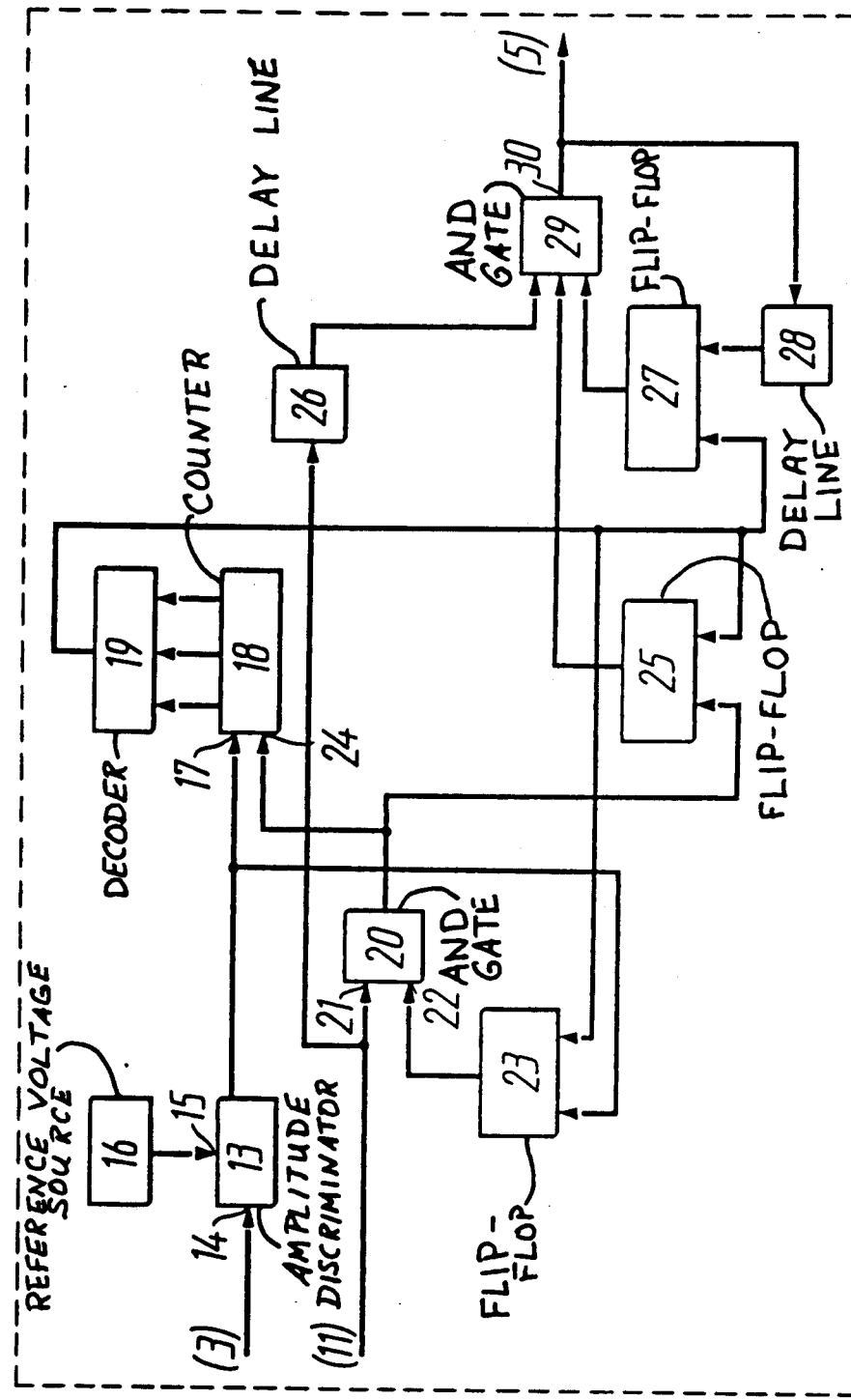
FIG. 2 is a block unit diagram of the shaper of single pulses in the apparatus embodying the invention.

The shaper 4 (FIG. 2) of single pulses includes an amplitude discriminator 13 of which the first input 14 serves as the input of the shaper 4 of single pulses, connected to the output of the amplifier 3 of electric signals. The other input 15 of the shaper 4 is connected to receive a discrimination threshold signal from a reference voltage source 16. The output of the amplitude discriminator 13 is connected to the reset input 17 of a counter 18 having its outputs connected to the inputs of a decoder 19. The shaper 4 of single pulses further includes an AND gate 20 having its first input 21 connected to receive clock pulses from the clock pulse generator 11, its second input 22 connected to the output of a flip-flop 23, and the output connected to a counting input 24 of the counter 18 and a first input of a flip-flop 25. The input 21 of the AND gate 20 is also connected to the input of a delay line 26. The flip-flop 23 has its first input connected to the output of the amplitude discriminator 13. Second inputs of the flip-flops 23 and 25 are connected to the output of the decoder 19. The shaper 4 of single pulses still further includes a flip-flop 27 having its first input connected to the output of the decoder 19 and its second input connected to the output of a delay line 28. Respective outputs of the delay line 26 and flip-flops 25, 27 are connected to the first, second and third inputs of an AND gate 29. The output 30 of the AND gate 29 is connected to the input of the delay line 28 and serves as the output of the shaper 4 of single pulses.

Figure 3:
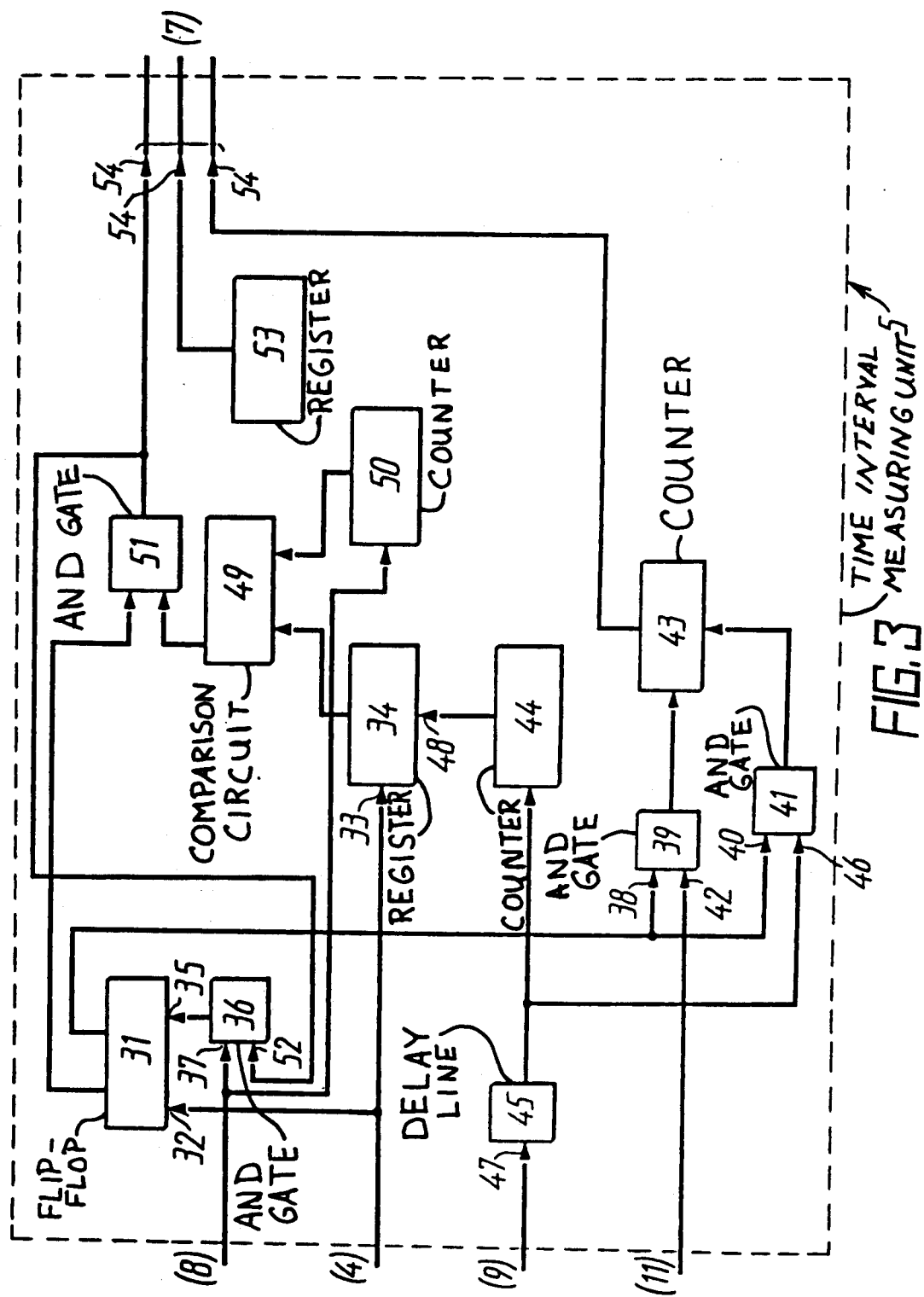
FIG. 3 is a block unit diagram of the unit for measuring time intervals in the apparatus embodying the invention.

The unit 5 (FIG. 3) for measuring time intervals includes a flip-flop 31 of which the first input 32 is connected to the first WRITE input 33 of a register 34 and serves as the first input of the unit 5, connected to the output of the shaper 4 of single pulses. The other input 35 of the flip-flop 31 is connected to the output of an AND gate 36 having its first input 37 connected to receive a reset signal from the output of the computer 8. One output of the flip-flop 31 is connected to the first input 38 of an AND gate 39 and to the first input 40 of an AND gate 41. The other input 42 of the AND gate 39 serves as the second input of the unit 5, connected to the output of the clock pulse generator 11. The outputs of the AND gates 39, 41 are connected, respectively, to the count input and reset input of a counter 43.

The unit 5 further includes a counter 44 having its count input connected to the output of a delay line 45. The output of the delay line 45 is also connected to the second input 46 of the AND gate 41. The input 47 of the delay line 45 serves as the third input of the unit 5 for measuring time intervals, connected to the output of the OR gate 9.

The output of the counter 44 is connected to the data input 48 of the register 34. The output of the register 34 is connected to the first input of a comparison circuit 49. The second input of the comparison circuit 49 is connected to the output of a counter 50 having its input connected to the input 37 of the AND gate 36. The unit 5 still further includes an AND gate 51 having its first input connected to the second output of the flip-flop 31, its second input connected to the output of the comparison circuit 49, and its output connected to the input of an AND gate 52. The unit 5 also includes a channel number register 53. The outputs of the counter 43, of the AND gate 51 and of the channel number register 53 form the output 54 of the unit 5 for measuring time intervals, connected to the input of the switching device 7.

Figure 4:
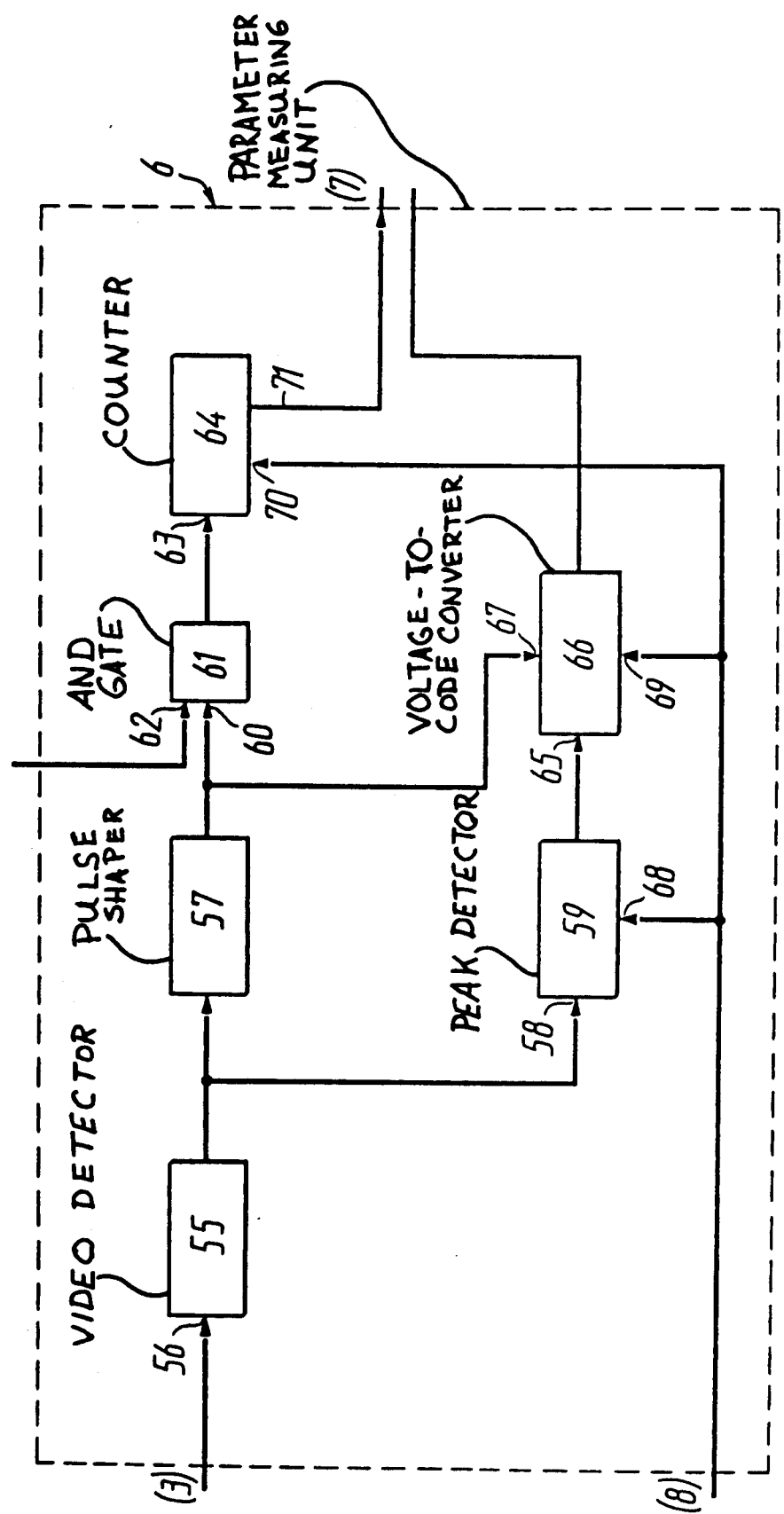
FIG. 4 is a block unit diagram of the unit measuring the parameters of acoustic emission signals in the apparatus embodying the invention.

The unit 6 (FIG. 4) for measuring the parameters of acoustic emission signals includes a video detector 55 of which the input 56 serves as the input of the unit 6, connected to the output of the amplifier 3 of electric signals. The output of the video detector 55 is connected to the input of a pulse shaper 57 and to the first input 58 of a peak detector 59. The output of the pulse shaper 57 is connected to the first input 60 of an AND gate 61 having its second input 62 connected to receive clock pulses from the clock pulse generator 11. The output of the AND gate 61 is connected to the count input 63 of a counter 64. The output of the peak detector 59 is connected to the first measurement input 65 of a voltage-to-code converter 66 of which the second control input 67 is connected to the ouput of the pulse shaper 57. The second input 68 of the peak detector 59, the third input 69 of the voltage-to-code converter 66 and the second (reset) input 70 of the counter 64 are connected to receive CLEAR signals from the computer 8. The output 71 of the counter 64 and the output of the voltage-to-code converter 66 form the output of the unit 6 for measuring parameters of acoustic emission signals, connected to the input of the switching unit 7.

Figure 5:
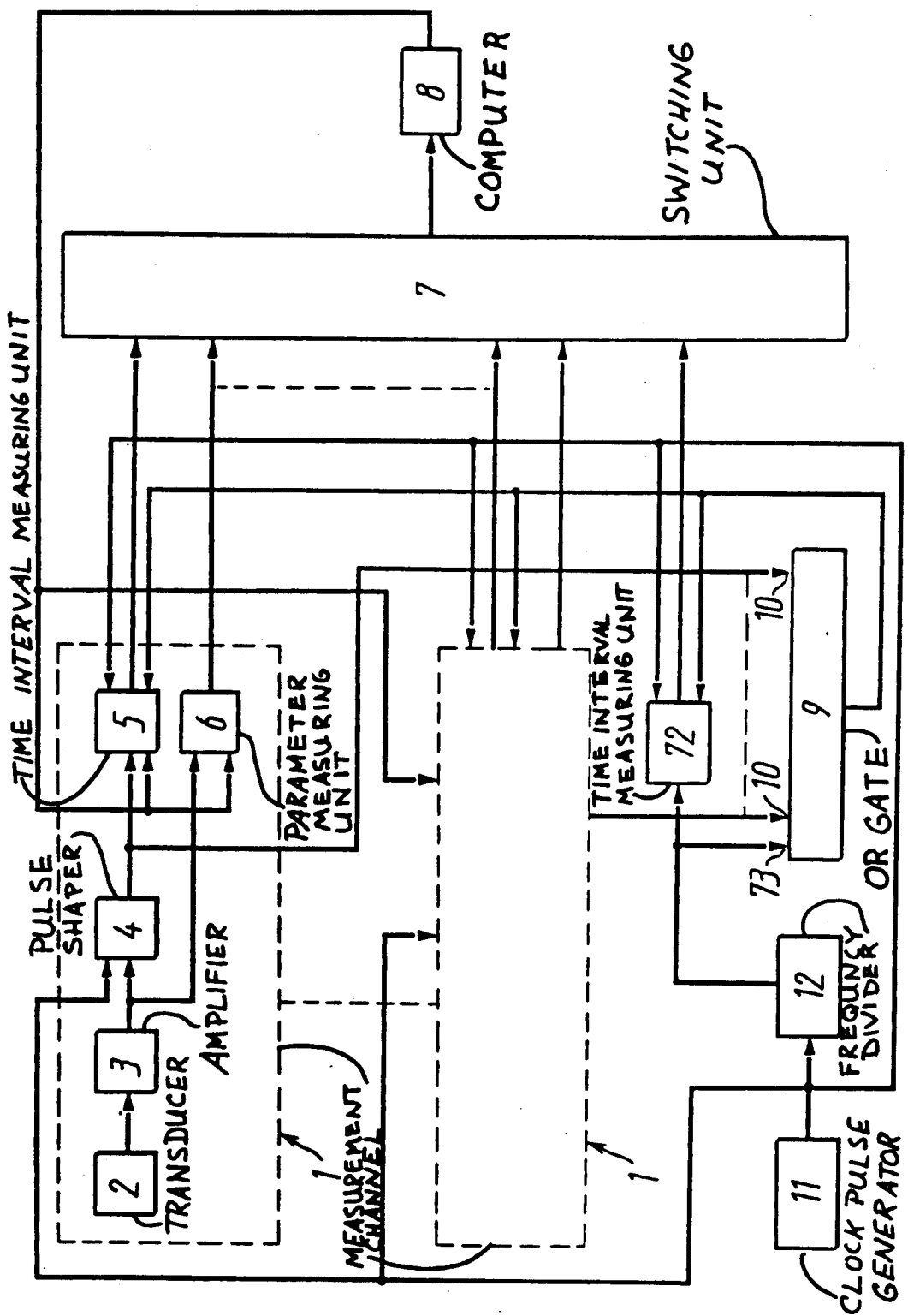
FIG. 5 is the block unit diagram of another embodiment of the apparatus according to the invention.

The modified embodiment of the apparatus for acoustic-emission inspection of articles, according to the present invention, schematically illustrated in FIG. 5 additionally comprises a unit 72 (FIG. 5) for measuring time intervals, having its first input connected to the output of the frequency divider 12 and to the additional input 73 of the OR gate 9, its second input connected to the output of the clock pulse generator 11, and its third input connected to the output of the OR gate 9. The output of the unit 72 is connected to the switching device 7. Structurally, the additional unit 72 for measuring time intervals is similar to the unit 5 described hereinabove.

The disclosed apparatus for acoustic-emission inspection of articles operates, as follows.

The evolution and development of cracks and strained areas in the structure of an article yield waves of acoustic emission responded to by the transducers 2 (FIG. 1) fastened to the surface of the article, which convert them into electric signals (FIGS. 6 $a$, $b$, $c$) having their amplitudes amplified by the amplifiers 3 in the respective channels 1. The parameters of these signals (i.e. the maximum amplitude and duration) are measured in the respective units 6 measuring the parameters of these signals of acoustic emission.

The video detector 55 (FIG. 4) of the unit 6 shapes the envelope of the signal of acoustic emission (FIG. 7a). In measuring the duration of a signal, the pulse shaper 57 (FIG. 4) generates a signal of a preset amplitude (FIG. 7b) strobing the passage of clock pulses from the clock pulse generator 11 (FIG. 4) to the counter 64. Thus, the code value at the output of the counter 64 is proportional to the duration of the signal at the input of the measuring unit 6. The output signal of the video detector 55 is fed to the peak detector 59 which feeds out a potential (FIG. 7c) of a value equalling the maximum amplitude of its input signal. This signal is converted into a binary code by the voltage-to-code converter 66 (FIG. 4), delivered jointly with the signal duration code to the output of the unit 6. The ensuing reset pulse resets the counter 64, the storage components of the voltage-to-code converter 66 and the peak detector 59.

The output of each amplifier 3 (FIG. 1) feeds out the acoustic emission signals also to the input of the shaper 4 of single pulses, intended to recover the acoustic emission signals against the background noise and to shape by their fronts the new pulses of preset duration and amplitude (FIGS. 6d, e, f). The presetting of the signals by amplitude is performed by means of the amplitude discriminator 13 (FIG. 2) of the shaper 4, and the presetting of the signals by duration is performed by means of the digital components of the shaper 4 of single pulses.

In this, the pulses from the output of the amplitude discriminator 13 set the counter 18 to "0" state, and the flip-flop 23 to "1" state. The first clock pulse coming from the clock pulse generator 11 sets the flip-flop 25 to "1" state, and a clock pulse delayed by the delay line 26 is produced at the output of the AND gate 29, setting, through the delay line 28, the flip-flop 27 to "0", and thus inhibiting the passage of successive clock pulses to the input of the single pulse shaper 4. Then, the counter 18 counts the clock pulses, and if no pulse comes from the output of the amplitude discriminator 13 over a given period, the decoder 19 reacts, setting the flip-flops 23 and 25 to "0" and the flip-flop 27 to "1". Alternatively, if pulses come during this given period from the output of the amplitude discriminator 13, they reset the counter 18 to start once again the counting of the required pause between the pulses.

The level of discrimination is set so as to recover useful acoustic emission signals against background noise.

The time intervals $\Delta t$ between pulses coming from the outputs of the respective single pulse shapers 4 of the individual channels 1 are converted into binary code in the respective units 5 (FIG. 3) for measuring time intervals, with each time interval $\Delta t_i$ (FIG. 6h) beginning from the instant of reception of the preceding signal of acoustic emission in either channel 1 (FIG. 1)—the output signal of the OR gate 9—and ending with the instant of reception of the next signal by this channel 1 (FIGS. 6d, e, f)—the signal at the output of the single pulse shaper 4. The time interval $\Delta t_i$ (FIG. 6h) is measured by the counter 43 (FIG. 3) by counting clock pulses coming to its input 42 from the clock pulse generator 11. The counter 43 starts its up-count the moment it is reset to "0" by a pulse coming from the output of the OR gate 9 to the input 47 of the delay line 45 of the unit 5.

The delay line 45 is intended to eliminate ambiguous situations caused by simultaneous application of pulses to the first input of the unit 5 from the single pulse shaper 4 and to the third input of the unit 5 from the output of the OR agate 9. The counter 43 stops counting when the input of the AND gate 39 receives a potential formed at the flip-flop 31 receiving at its one input 32 a pulse from the output of the single pulse shaper 4 and at its other input 35, via the AND gate 36, a reset pulse. Thus, a reset pulse is produced by the computer 8 when it receives data from the channel 1 via the switching unit 7. Beside the value of the time interval, also delivered from the register 53 to the output of the unit 5 for measuring time intervals is the consecutive number of the channel 1 to which this unit 5 belongs.

Simultaneously with the reception of a pulse from the shaper 4 of single pulses of the given channel 1, the code fed from the output of the counter 44 which counts pulses received from the output of the OR gate 9 is entered to the register 34. The counter 50 counts the successive CLEAR pulses. When the codes (readings) of the register 34 and counter 50 are the same, the comparison circuit 49 responds, and if the flip-flop 31 is in state "1", i.e. an acoustic emission signal has been received by the given channel 1, there is formed a signal enabling transfer of the data from this channel 1 via the switching unit 7 into the computer 8. Thus, in the transmission of information from the channels 1 to the computer 8, there is maintained the order in which these channels 1 have been receiving the signals of acoustic emission. This provides for the maximum efficiency and simplicity of the algorithm of computation in the computer 8 of the time intervals between signals coming from different channels 1, which are necessary for calculating the coordinates of the source of acoustic emission.

The repetition rate (recurrence rate) of clock pulses is selected to ensure the required accuracy of the counting of the time intervals between signals of acoustic emission. The frequency divider 12 produces, from the recurrent pulses coming from the clock pulse generator 11, a sequence of time marker signals (FIG. 6g).

A time marker signal is directly supplied to the switching device 7 and, further, to the computer 8. The time marker signals have a preset amplitude, their duration corresponding to the duration of the clock pulses like the duration of output pulses of the single pulse shaper 4).

As the time marker signal is not synchronized with the signals of acoustic emission, the position of the last-mentioned signals in the computer 8 can be determined with the accuracy determined by the consecutive number of a time marker.

In the embodiment of the disclosed apparatus shown in FIG. 5, a time marker signal passes through the OR gate 9 to the third inputs of all the units 5 and of the unit 72, and also to the first input of the unit 72, initiating therein the same processes that are initiated in the units 5 by the signals coming from respective single pulse shapers 4.

However, the additional unit 72 for measuring time intervals produces, not the channel number code, but a time marker indicator encoded with a predetermined numeral, e.g. "0". Thus, in the embodiment illustrated in FIG. 5 a time marker signal is introduced into the computer 8 via the switching unit 7 in synchronism with the acoustic emission data. With the position of a time marker signal being fixed with respect either to the last-received acoustic emission signal or to the preceding time marker, and the position of the next-received acoustic emission signal being fixed with respect to this (current) time marker signal, the recurrence rate of the time marker signals is selected from an expression:

$$f = \frac{f_t}{2^k},$$

where $f_t$ is the recurrence rate (frequency) of clock pulses; and k is the digit (word) length of the time intervals measured in the units 5 and 72.

This embodiment of the disclosed apparatus determines the time-related position of each occurrence of acoustic emision with the accuracy of the recurrence period of clock pulses. Thus, in a prototype of the apparatus being described, the frequency of clock pulses is $f_t = =1$ MHz, and the recurrence rate of the time marker signals is $f = 16$ Hz (the divider 12 gives a $2^{16}:1$ countdown). The information supplied to the computer 8 includes the channel number code, the time marker indicating code, time intervals $\Delta t_i$ between the signals of acoustic emission and time markers, and the values of the parameters of the acoustic emission signals. The computer 8 computes time intervals between the signals of acoustic emission, necessary for the computation of the coordinates of their sources, which is carried out by summing up the measured values $\Delta t_i$, $\Delta t_{i+1}$, $\Delta t_{i+2}$, $\Delta t_{i+3}$ (FIG. 6g).

Then the computer 8 calculates the coordinates of the sources of acoustic emission. Thus, for a group of four transducers 2 arranged on the article under inspection at the corners and center of an equilateral triangle, the Cartesian coordinates of the source of acoustic emission are computed from an expression:

$$x = \frac{r_1 r_3(r_3 - r_1) + r_1 r_2(r_1 - r_2) + (B^2 + 2r_2 r_3)(r_3 - r_2) + 3r_4[r_3(r_4 - r_3) + r_2(r_2 - r_4)]}{2B(r_1 + r_2 + r_3 - 3r_4)}$$

$$y = \frac{(3r_1 r_3 + B^2)(r_3 - r_1) + (3r_1 r_2 + B^2)(r_2 - r_1) + 3R_4[2r_1(r_1 - r_4) + r_2(r_4 - r_2) + r_3(r_4 - r_3)]}{2\sqrt{3}\, B(r_1 + r_2 + r_3 - 3r_4)}$$

where $r_j = \Delta t_j V (j = 1, 2, 3, 4);$ where $\Delta t_j$ are the computed values of the time intervals with respect to the transducer which has been the first to register the signal (for this transducer, $\Delta t$ equals zero);

V is the rate of propagation of acoustic emission signal in the article under inspection; and B is the spacing of the transducers of acoustic emission signals.

Then the computer 8 calculates the energy characteristics of the accoustic emission sources from a formula:

$$E_s = \sum_2 A_1^2 T_1$$

where

S is the successive number of the source;

l is the number of the occurrence of acoustic emission;

A is the maximum amplitude of the signal of acoustic emission, and

T is the duration of the signal of acoustic emission.

The values $E_s$ thus computed are used to determine the potential hazard from the S-th source of acoustic emission, e.g. from a developing crack.

Thus, the employment of the present invention provides for enhancing the reliability of inspection of articles with high levels of acoustic emission activity. The disclosed apparatus provides for determination of the time of occurrence of the acoustic emission phenomena with a high accuracy, and thus for closely monitoring the dynamics of acoustic-emission processes in an article under inspection.

The present invention can be employed in the oil-and-gas and chemical industries for quality control and inspection of major pipeline, compressor units, offshore stationary platforms; in nuclear power engineering for testing and inspection of the reactors of nuclear power plants; in aircraft engineering for inspection of aircraft in flight and in the course of ground inspection and testing of the strength characteristics; in general engineering for inspection and testing of cranes, pressure vessels and other metal structures; in construction for quality control and inspection of bridges, towers and masts.

The suggested frequency of clock pulses is 0.5–2.0 MHz. The duration of clock pulses and time marker signals should be 100–200 μs.

It is also expedient that the digit capacity of the counters in the time interval measurement units 5, as well as of the counter in the unit 6 measuring the parameters of acoustic signals should be sixteen bits, and the word digit capacity of the voltage-to-code converter in the unit 6 measuring the parameters of acoustic emission signals should be twelve bits.

We claim:

1. An apparatus for acoustic-emission inspection of articles, comprising: channels each including a series connection of a transducer of acoustic emission signals, positionable on an article under inspection, and an amplifier of electric signals, having an output connected to a shaper of single pulses and to a unit for measuring parameters of acoustic emission signals, and also a clock pulse generator connected with each channel, a switching unit having inputs connected to outputs of the units for measuring the parameters of acoustic emission signals and also connected with the shapers of single pulses of respective channels, and a computer for processing acoustic-emission data, connected to the switching unit, further comprising, in each channel, a unit for measuring time intervals, having a first input connected to an output of the shaper of single pulses, a second input connected to an output of the clock pulse generator, and an output connected to the input of the switching unit, and also a frequency divider having an input connected to the output of the clock pulse generator and an output connected to the switching unit, and an OR gate having inputs in a number equalling the number of the channels, said inputs of said OR gate being connected to the respective outputs of the shapers of single pulses of each channel, and having an output connected to third inputs of the respective units for measuring time intervals in each channel.

2. An apparatus according to claim 1, further comprising: an additional unit for measuring time intervals, having a first input connected to an output of the frequency divider and to an additional input of the OR gate, a second input connected to the output of the clock pulse generator, a third input connected to the output of the OR gate, and an output connected to the input of the switching unit.

* * * * *